United States Patent [19]

Sakaniwa et al.

[11] Patent Number: 5,155,757
[45] Date of Patent: Oct. 13, 1992

[54] X-RAY DIAGNOSING APPARATUS

[75] Inventors: Hiroshi Sakaniwa, Ootawara; Satoshi Ohta, Imaichi, both of Japan; Katsuhiko Koyama, Irvine, Calif.

[73] Assignee: Kabushiki Kaisha Toshiba, Kawasaki, Japan

[21] Appl. No.: 718,300

[22] Filed: Jun. 20, 1991

[30] Foreign Application Priority Data

Jun. 20, 1990 [JP] Japan .................................. 2-159805
Jun. 20, 1990 [JP] Japan .................................. 2-159806

[51] Int. Cl.$^5$ ............................................. H05G 1/02
[52] U.S. Cl. ..................................... 378/197; 378/196
[58] Field of Search ......................... 378/197, 195, 196

[56] References Cited

U.S. PATENT DOCUMENTS 5,038,371 8/1991 Janssen .................................. 378/197

Primary Examiner—Craig E. Church
Attorney, Agent, or Firm—Oblon, Spivak, McClelland, Maier & Neustadt

[57] ABSTRACT

An x-ray diagnosing apparatus includes a holding unit including an x-ray source, an x-ray image detector, an a rotating/driving unit for integrally rotating the x-ray source and the x-ray image detector about first, second, and third axes which are perpendicular to each other, sensors for detecting rotational angles with respect to the first, second, and third axes, respectively, calculating unit for calculating clinically defined diagnostic angles by using the rotational angles detected by the detectors with respect to the first, second, and third axes, a memory for storing the diagnostic angles calculated by the calculating unit, and a control system for performing write control to write the diagnostic angles, of the holding unit in a photographing operation, in the memory, performing read control to read out the diagnostic angles from the memory in a re-photographing operation, and performing control to supply a command to the rotating/driving unit to set the holding unit in the same state as the photographing operation by using the diagnostic angles read out by the read control.

8 Claims, 8 Drawing Sheets

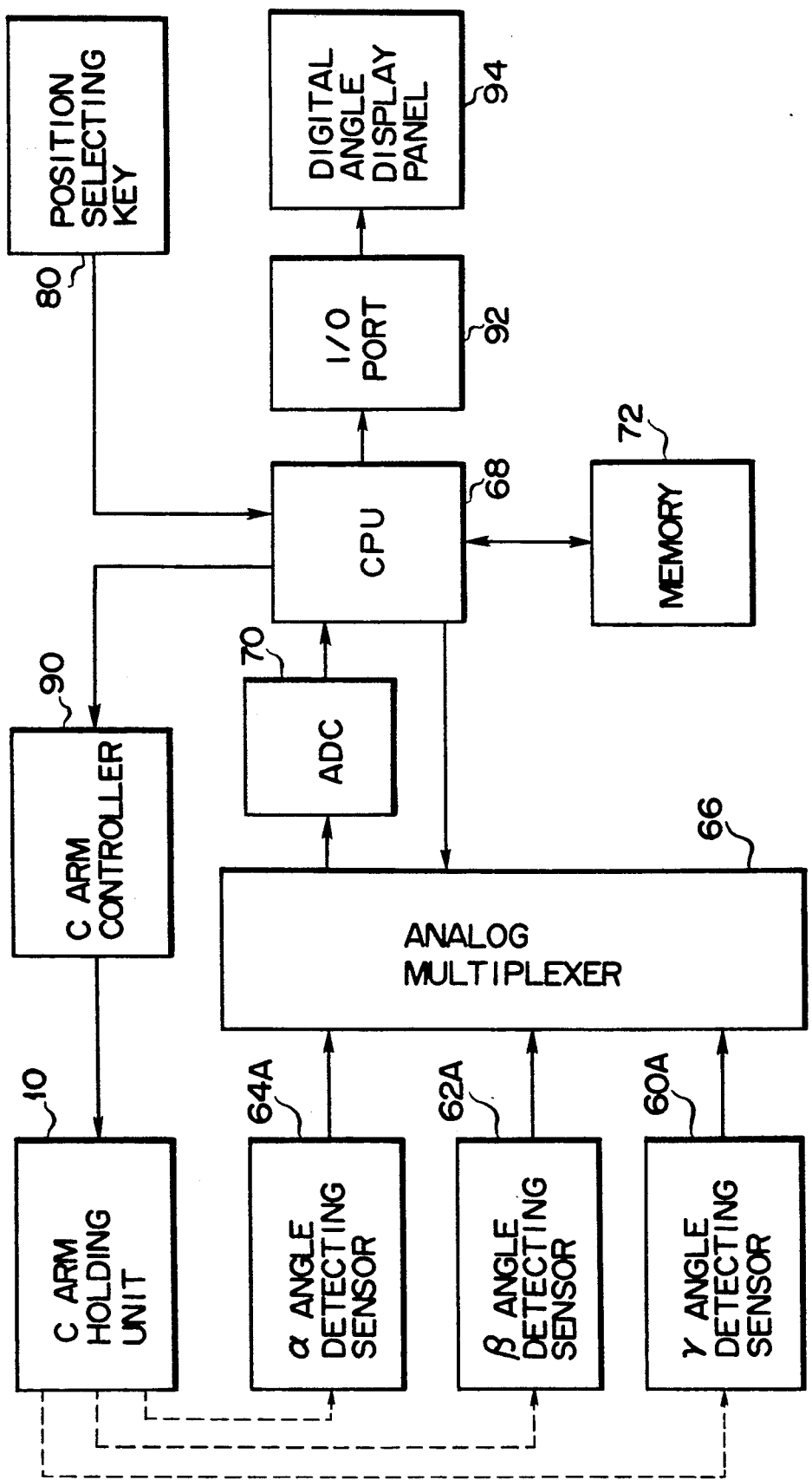
F I G. 8

X-RAY DIAGNOSING APPARATUS

BACKGROUND OF THE INVENTION

1. Field of the Invention

The present invention relates to an x-ray diagnosing apparatus in which x-rays which are radiated from an x-ray source and transmitted through an object to be examined are converted into an optical image by an image intensifier, and the optical image is input to a TV camera to display a fluoroscopic image on a TV monitor, or the optical image is used to perform photography by using an x-ray film.

2. Description of the Related Art

In general, a C- or U-shaped arm type holding unit is used in an x-ray diagnosing apparatus for angiography of an object to be examined. For example, a C arm type holding unit is designed such that an x-ray tube is fixed to one end of a C-shaped C arm, and an image intensifier (to be referred to as an I.I. hereinafter) is fixed to the other end of the C arm to oppose the x-ray tube. The I.I. is used to convert x-rays, radiated from the x-ray tube and transmitted through an object to be examined, into an optical image. Note that other arm type holding units having shapes other than C and U shapes are sometimes used. When angiography of the object is to be performed, the x-ray tube and the I.I. arranged on the two ends of the C arm of the holding unit must be set at proper angles with respect to a portion, of the object, to be subjected to fluoroscopy (or a portion to be photographed).

In angiography of an object, first, second, and third axes which are defined in advance are used. These axes are perpendicular to each other. The first axis is the body axis indicating the direction of the head and lower limbs of the object. The first axis is generally called the X axis. The second axis is an axis which is perpendicular to the body axis and indicates the direction of the width of the shoulders. The second axis is generally called the Y axis. The third axis is a vertical axis which is perpendicular to the body axis and passes through the isocenter. The third axis is generally called the Z axis. Of these axes, the Z axis is used as a reference, and the other two axes are adjusted with respect to the Z axis to perform angle setting operations in photography. More specifically, the C arm of the holding unit is rotated about the X axis as a rotation center to be set at an angle $\beta$ (arm rotational angle $\beta$), and is rotated about the Y axis as a rotation center to be set at an angle $\alpha$ (slide angle $\alpha$). These angle setting operations are performed by an angle setting section. These set angles are stored in a memory. Therefore, when the second and subsequent photographing operations are to be performed, the photographing angle data is read out from the memory to reproduce the previous photographing direction.

In photography of blood vessels of the object with a contrast medium, diagnostic angles which are clinically defined are used independently of angles associated with the holding unit (to be referred to as mechanical angles hereinafter), such as the slide angle $\alpha$ and the arm rotational angles $\beta$. Diagnostic angle $\theta$ and $\eta$ are defined as follows:

$\theta$ = LAO/RAO
$\eta$ = CRA/CAU where LAO and RAO correspond to the arm rotational angle $\beta$. More specifically, LAO is a counterclockwise rotational angle of the arm rotational angle $\beta$, and RAO is a clockwise rotational angle of the arm rotational angle $\beta$. In addition, CRA is an abbreviation for "cranial"; and CAU, "caudal". CRA and CAU correspond to the slide angle $\alpha$. More specifically, CRA is a rotational angle of the slide angle $\beta$ in the direction of the head, and CAU is a rotational angle of the slide angle $\beta$ in the direction of the lower limbs.

While diagnostic and mechanical angles coincide with each other, the slide angle $\alpha$ is identical to the diagnostic angle $\eta$, and the rotational angle $\beta$ is identical to the diagnostic angle $\theta$. This state is displayed on a display unit.

According to a recent 3-axis control type holding unit, a rotating operation with the Z axis being set as a reference can be performed, in addition to rotating operations with the X and Y axes being set as references. If used, an angle setting operation can be quickly performed to locate the arm at the optimal position with respect to an object to be examined. This, for example, facilitates a tracking operation with respect to a blood vessel.

FIG. 1 is a front view showing an x-ray diagnosing apparatus including a 3-axis control type holding unit. A 3-axis control type holding unit 10 includes a column (Z axis) rotation axis 30 for setting a column rotational angle $\gamma$ as a mechanical angle, a spindle (Y axis) rotation axis 32 for setting an arm rotational angle $\beta$ as a mechanical angle, and an (X axis) slide axis 34 for setting a slide angle $\alpha$ as a mechanical angle. The slide angle $\alpha$, the arm rotational angle $\beta$, and the column rotational angle $\gamma$ can be set by a controller (not shown).

While the column rotational angle y is set to be 0, a C arm 16 is positioned at the head and abdomen of an object 200 to be examined. If a state "A" shown in FIG. 1 is set, a slide angle $\alpha_1$ coincides with a diagnostic angle $\eta$, and an arm rotational angle $\beta_1$ coincides with a diagnostic angle $\theta$.

If, however, the column rotational angle $\gamma$ is set to be 90° to position the C arm 16 at the lower limbs of the object 200, i.e., if a state "B" in FIG. 1 is set, a slide member 16B is moved on the slide axis 34, and the spindle (Y axis) rotation axis 32 is also rotated. As a result, the slide angle $\alpha$ and the arm rotational angle $\beta$ are changed from the initial angles. That is, since the number of axes (degrees of freedom) of the 3-axis control type holding unit 10 is larger than that of a 2-axis control type holding unit by one, a slide angle $\alpha_3$ and an arm rotational angle $\beta_3$ do not coincide with the diagnostic angles $\eta$ and $\theta$, respectively.

In addition, this inaccurate diagnostic angle $\theta$ is stored in a memory. For this reason, even if the diagnostic angle is read out from the memory, in a rephotographing operation, to be used for positioning for photography, the previous photographing direction cannot be reproduced. Under the circumstances, it takes much time to reproduce an accurate angle setting operation, resulting in an increase in operation load of an operator. Furthermore, changes in column rotational angle $\gamma$ cause rotation of an image. Such inconvenience can be eliminated, i.e., the image can be corrected, by also rotating a TV camera attached to an I.I. 20. However, since a film changer 22 and a cinematic camera are mounted on the I.I. 20 together with the TV camera, a mechanism for rotating these components is required. As a result, the apparatus is complicated.

SUMMARY OF THE INVENTION

It is an object of the present invention to provide an x-ray diagnosing apparatus including a 3-axis control type holding unit having high repeatability with respect to mechanical and diagnostic angles.

It is another object of the present invention to provide an x-ray diagnosing apparatus which can shorten the time required for examination and can reduce the operation load of an operator by improving repeatability in photography.

In order to achieve the above objects, according to the present invention, there is provided an x-ray diagnosing apparatus comprising:

a holding unit including x-ray generating means, x-ray image detecting means, and rotating/driving means for integrally rotating the x-ray generating means and the x-ray image detecting means about first, second, and third axes which are perpendicular to each other;

detecting means for detecting rotational angles with respect to the first, second, and third axes, respectively;

calculating means for calculating clinically defined diagnostic angles by using the rotational angles detected by the detecting means with respect to the first, second, and third axes;

storage means for storing the diagnostic angles calculated by the calculating means; and control means for performing write control to write the diagnostic angles, of the holding unit in a photographing operation, in the storage means, performing read control to read out the diagnostic angles from the storage means in a re-photographing operation, and performing control to supply a command to the rotating/driving means to set the holding unit in the same state as in the photographing operation by using the diagnostic angles read out by the read control.

In addition, in order to achieve the above objects, according to the present invention, there is provided an x-ray diagnosing apparatus comprising:

a holding unit including x-ray generating means, x-ray image detecting means, and rotating/driving means for integrally rotating the x-ray generating means and the x-ray image detecting means about first, second, and third axes which are perpendicular to each other;

mechanical angle detecting means for detecting rotational angles with respect to the first, second, and third axes, respectively;

calculating means for calculating clinically defined diagnostic angles by using the rotational angles detected by the mechanical angle detecting means with respect to the first, second, and third axes;

storage means for storing the diagnostic angles calculated by the calculating means;

control means for performing write control to write the diagnostic angles, of the holding unit in a photographing operation, in the storage means, and performing read control to read out the diagnostic angles from the storage means in a re-photographing operation; and display means for displaying the diagnostic angles read out from the control means.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 8 is a block diagram showing a control block of an x-ray diagnosing apparatus according to the second embodiment of the present invention;

DETAILED DESCRIPTION OF THE PREFERRED EMBODIMENTS

An x-ray diagnosing apparatus according to the first embodiment of the present invention will be described below.

Figure 1:
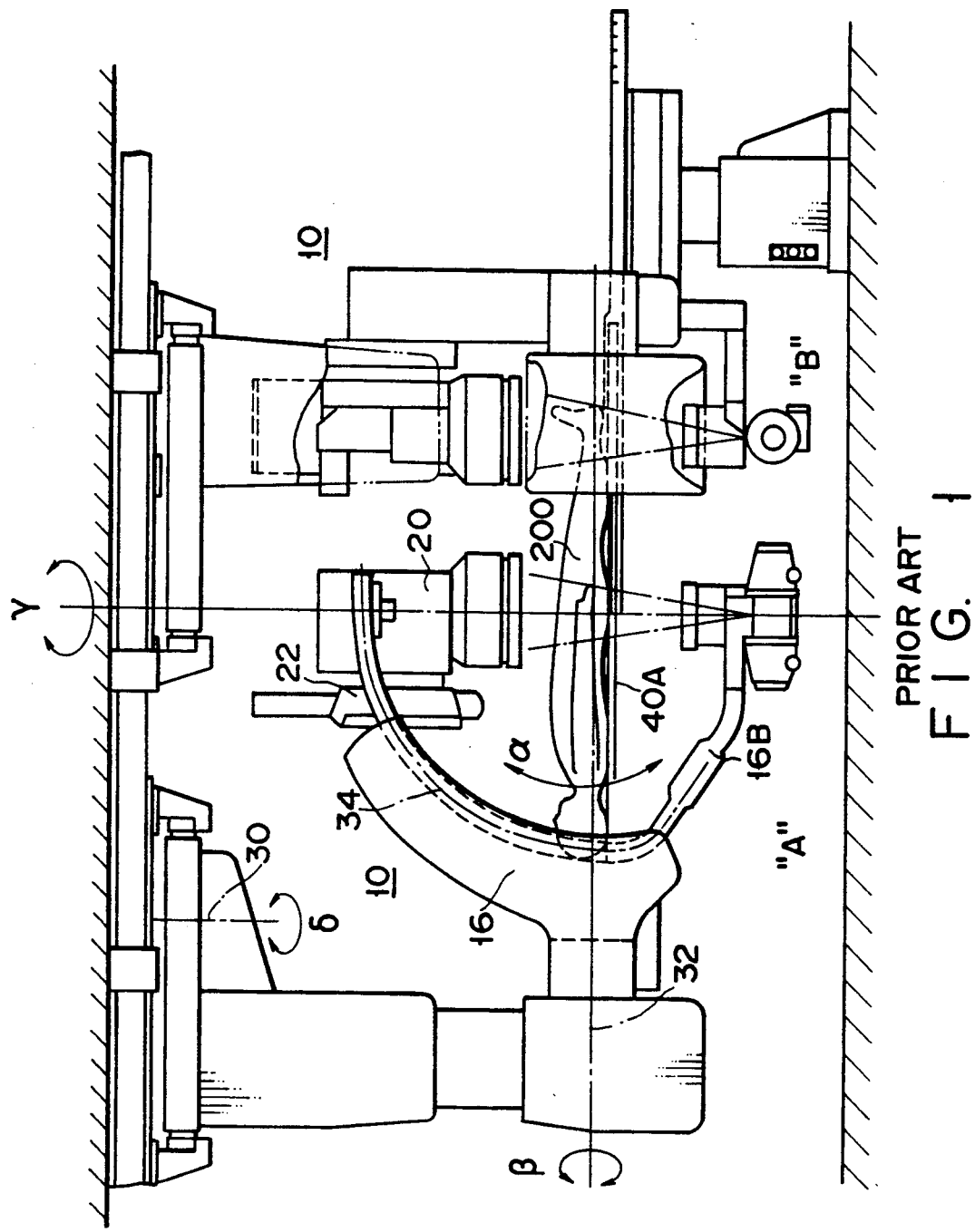
FIG. 1 is a front view showing a conventional x-ray diagnosing apparatus.
Figure 2:
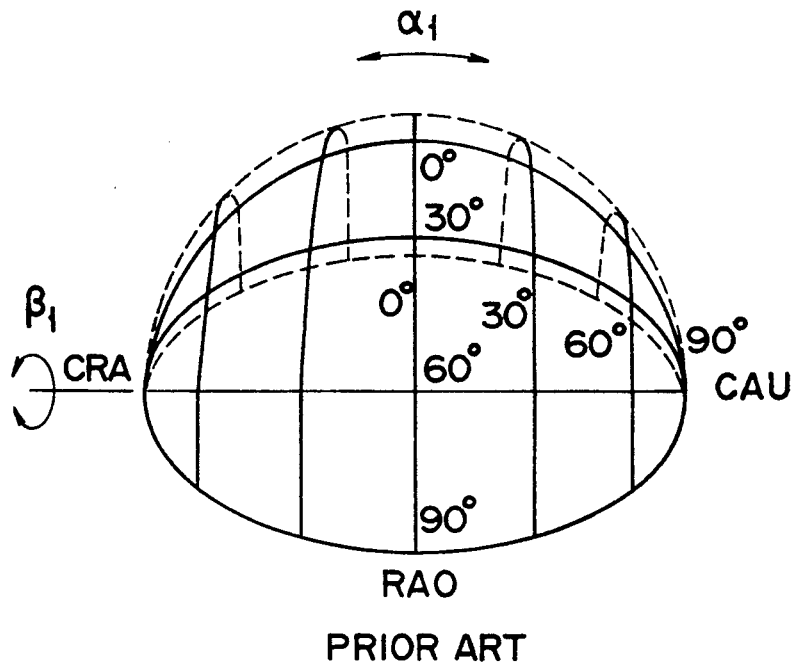
FIG. 2 is a view showing a relationship between mechanical and diagnostic angles in a case wherein a column rotational angle is set to be zero.
Figure 3:
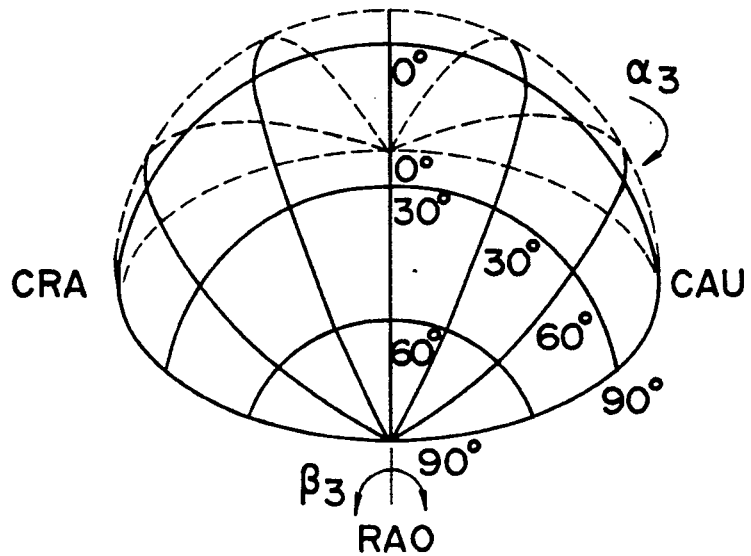
FIG. 3 is a view showing a relationship between mechanical and diagnostic angles in a case wherein a column rotational angle is set to be 90°.
Figure 4:
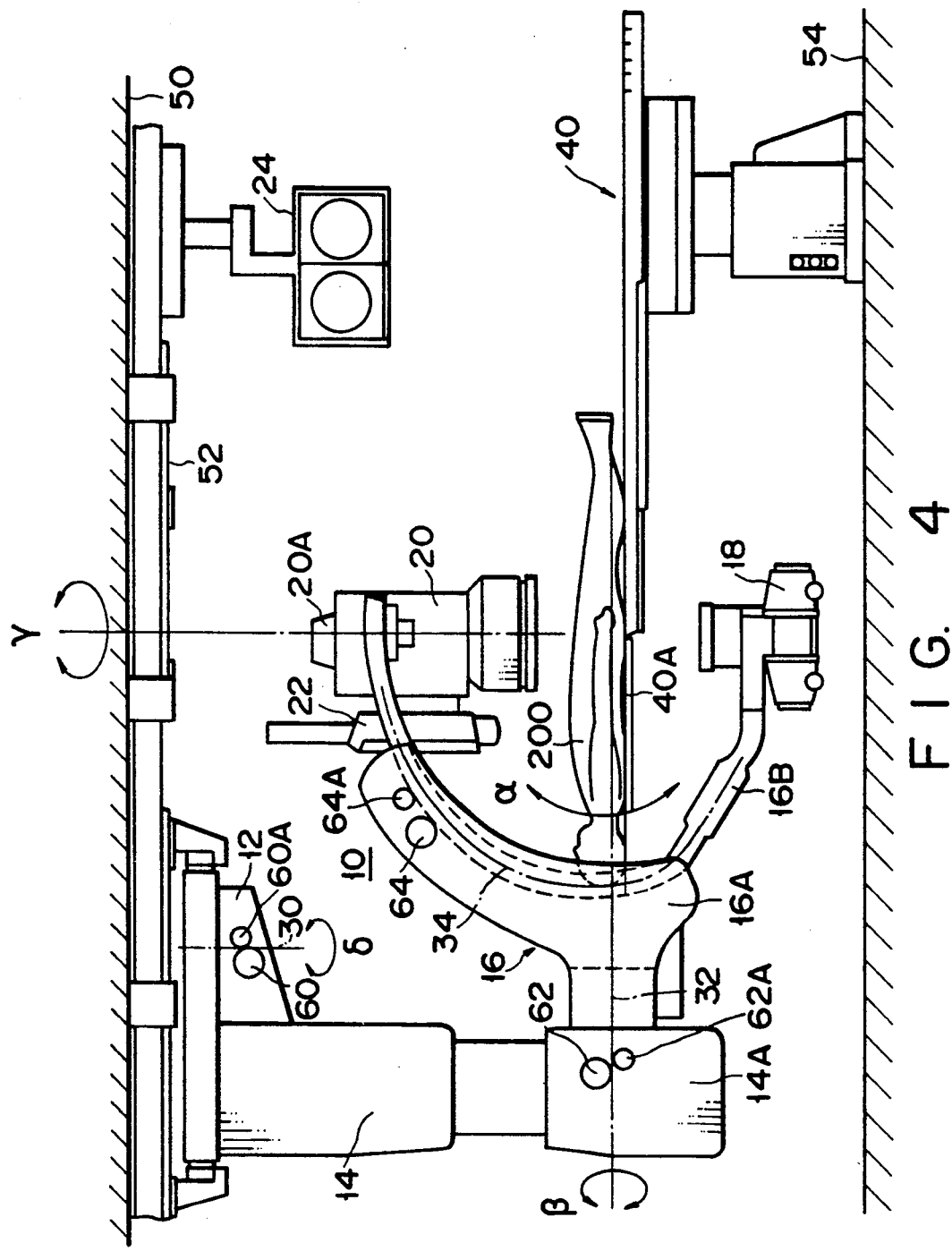
FIG. 4 is a front view showing an x-ray diagnosing apparatus according to the first embodiment of the present invention.

As shown in FIG. 4, the x-ray diagnosing apparatus includes a 3-axis control type holding unit 10. The 3-axis control type holding unit 10 is fixed in an examination room. The 3-axis control holding unit 10 includes a column rotation axis 30 for setting a column rotational angle $\gamma$ as a mechanical angle, a spindle rotation axis 32 for setting an arm rotational angle $\beta$ as a mechanical angle, and a slide axis 34 for setting a slide angle $\alpha$ as a mechanical angle. The holding unit 10 is movably arranged on rails 52 installed on a ceiling 50 in the X and Y directions. More specifically, the holding unit 10 has a base 12. A column 14 is vertically fixed to the base 12. The base 12 is movably arranged on the rails 52. The base 12 is provided with the column rotation axis 30. Therefore, the column 14 can be rotated in the direction indicated by an arrow in FIG. 4 about the axis 30 as a rotation center. With this rotating operation (Z-axis rotation), the mechanical angle $\gamma$ shown in FIG. 4 is set. That is, the column rotation angle $\gamma$ as a mechanical angle is set by a rotational angle $\delta$ with respect to the axis 30 as a rotation center. A C arm 16 is fixed to a side surface of a distal end portion 14A of the column 14. A connection portion between the distal end portion 14A of the column 14 and the C arm 16 is provided with the spindle rotation axis 32. Therefore, the C arm 16 can be rotated about the axis 32 as a rotation center in the direction indicated by an arrow ($\beta$) in FIG. 4. With this rotating operation, the arm rotational angle $\beta$ (X-axis rotation) as a mechanical angle shown in FIG. 4 is set. The C arm 16 is constituted by a slide base 16A and a slide member 16B which slides on the slide base 16A. With this arrangement, the slide member 16B has the slide axis 34 in relation to the slide base 16A. An x-ray tube 18 is fixed to the lower end of the slide member 16B while an I.I. 20 is fixed to the upper end of the slide member 16B to oppose the x-ray tube 18. The I.I. 20 includes a TV camera 20A. With this slide (rotation) operation, the slide angle $\alpha$ as a mechanical angle in FIG. 4 is set. Note that the slide member 16B includes a film changer for storing an x-ray film and a cinematic camera integrated with the I.I. 20. In addition, the x-ray diagnosing apparatus includes a TV monitor 24 for displaying a fluoroscopic image converted as an electrical signal output from the TV camera 20A. The TV monitor 24 is movably supported on the rails 52 by a support member 24. The TV monitor 24 may be directly fixed to the ceiling 50 or a wall.

A table unit 40 is fixed to a floor 54. An object 200 (to be examined) placed on a top plate 40A of the table unit 40 is located between the x-ray tube 18 and the I.I. 20.

A motor 60 is arranged in the base 12. The motor 60 serves to rotate the column 14 about the axis 30 as a rotation center. A motor 62 is arranged in the distal end portion 14A of the column 14. The motor 62 serves to rotate the C arm 16 about the axis 32 as a rotation center. A motor 62 is arranged in the slide base 16A. The motor 64 causes the slide member 16B to slide along the axis 34.

In addition, the base 12 incorporates a sensor 60A such as an encoder or potentiometer for detecting the column rotational angle $\gamma$, i.e., the rotational angle. The distal end portion 14A incorporates a sensor 62A such as an encoder or potentiometer for detecting the arm rotational angle $\beta$. The slide base 16A incorporates a sensor 64A such as an encoder or potentiometer for detecting the slide angle $\alpha$.

Figure 5:
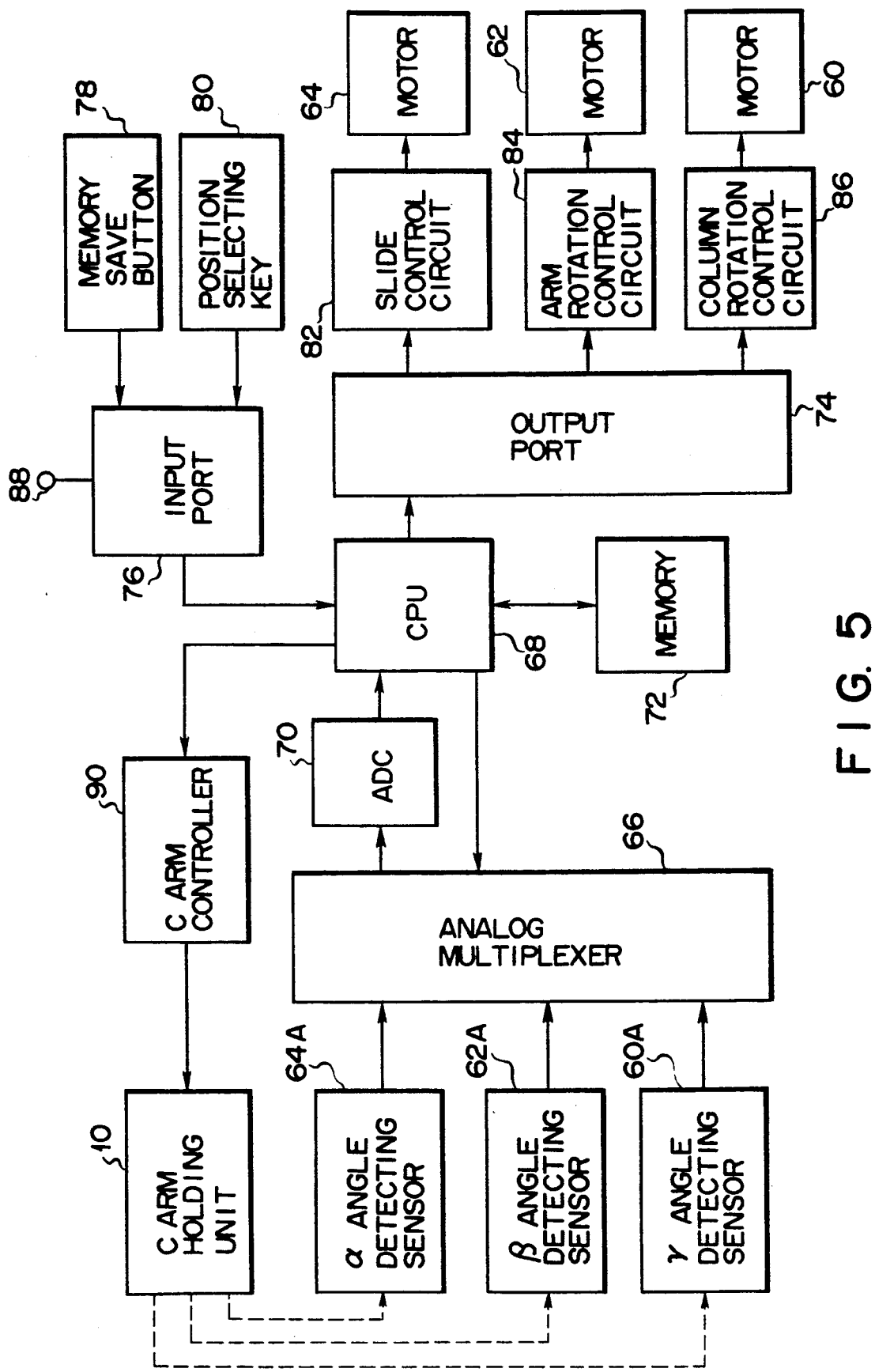
FIG. 5 is a block diagram showing a control block for controlling the apparatus in FIG. 1.

The x-ray diagnosing apparatus of this embodiment has the control circuit shown in FIG. 5 in addition to the main body portion shown in FIG. 4. More specifically, an analog multiplexer 66 receives the mechanical angles $\alpha$, $\beta$, and $\gamma$ detected by the sensors 60A, 62A, and 64A. The analog multiplexer 66 synthesizes the mechanical angles $\alpha$, $\beta$, and $\gamma$ in accordance with a control signal supplied from a CPU 68, and supplies the resultant value to an A/D converter (ADC) 70. The CPU 68 calculates diagnostic angles $\theta$ ($\theta$=LAO/RAO) and $\eta$ ($\eta$=CRA/CAU), which are displayed, by using the mechanical angles $\alpha$, $\beta$, and $\gamma$ output from the A/D converter 70 as digital values, according to equations (1) to (4):

$$\theta = \tan^{-1} b / \sqrt{1 - (a^2 + b^2)} \tag{1}$$

$$\eta = \sin^{-1} a \tag{2}$$

$$a = \sqrt{\sin^2\alpha + \cos^2\alpha \cdot \sin^2\beta} \cdot \cos\{\gamma + \sin^{-1}(\sin\beta/\tan\alpha)\} \tag{3}$$

$$b = \sqrt{\sin^2\alpha + \cos^2\alpha \cdot \sin^2\beta} \cdot \sin\{\gamma + \tan^{-1}(\sin\beta/\tan\alpha)\} \tag{4}$$

Figure 6:
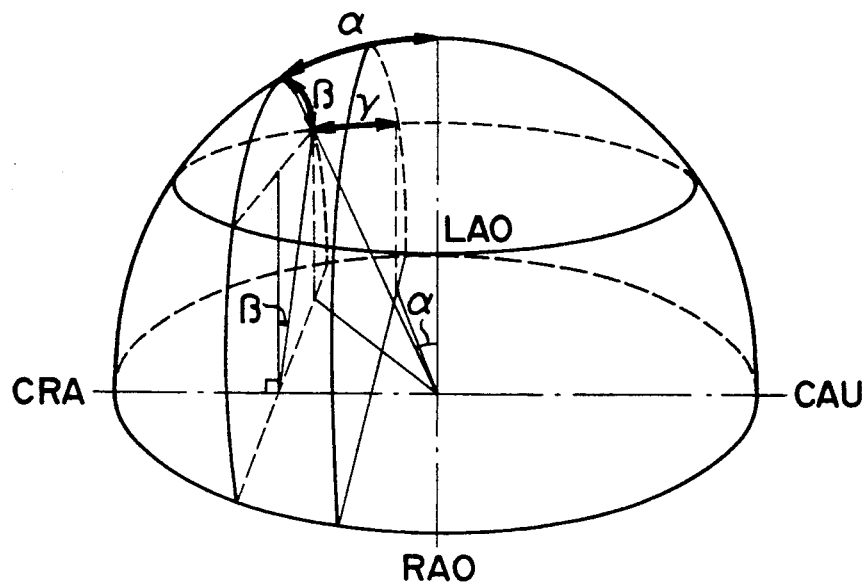
FIGS. 6 and 7 are views for explaining a method of obtaining diagnostic angles by using the apparatus shown in FIG. 4.
Figure 7:
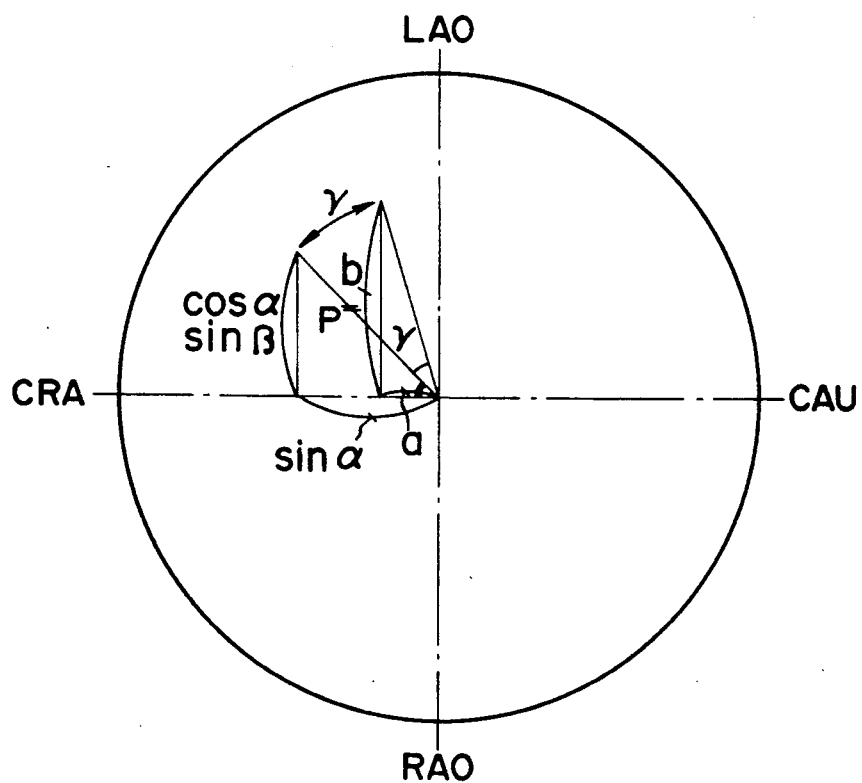

FIGS. 6 and 7 are a perspective view and a plan view, respectively, for explaining a method of obtaining the diagnostic angles $\theta$ and $\eta$. A memory 72 has a table for storing the diagnostic angles $\theta$ and $\eta$ obtained with respect to the mechanical angles $\alpha$, $\beta$, and $\gamma$ by using the above equations, provided that the CPU 68 is a 8-bit type or the like. The CPU 68 performs write and read control of diagnostic angles with respect to the memory 72 and supplies read diagnostic angles to an output port 74. An input port 76 supplies a command signal and angle setting data to the CPU 68. The command signal is used to command the memory 72 to save the stored diagnostic angles $\theta$ and $\eta$. The angle setting data is output from a position selecting key 80 and is used for a photographing position. A slide control circuit 82 rotates the motor 64 in accordance with the slide angle $\alpha$ output from the output port 74. An arm rotation control circuit 84 rotates the motor 62 in accordance with the arm rotational angle $\beta$ output from the output port 74. A column rotation control circuit 86 rotates the motor 60 in accordance with the column rotational angle $\gamma$ output from the output port 74. A C arm controller 90 which receives a command from the CPU 68 and controls a driving operation of the C arm holding unit 10 in relation to the mechanical angles $\alpha$, $\beta$, and $\gamma$. A reset button 88 is connected to the input port 76.

An operation of the apparatus of this embodiment having the above-described arrangement will be described below. A case wherein no $\delta$ rotation is performed will be described first. When no $\delta$ rotation is performed, the slide angle c and the arm rotational angle $\beta$ respectively coincide with the diagnostic angles $\eta$ and $\theta$. Therefore, the diagnostic angles $\theta$ and 72 calculated by the CPU 68 are stored in the memory 72. The CPU 68 reads out the diagnostic angles $\theta$ and $\eta$ from the memory 17 and supplies them to the control circuits 82, 84, and 86, respectively, through the output port 18. Subsequently, the motors 60, 62, and 64 are respectively rotated by the control circuits 82, 84, and 86 in accordance with the diagnostic angles coinciding with the mechanical angles $\alpha$ and $\beta$. With this operation, an angle setting operation is performed to locate the C arm 16 to a predetermined photographing position.

A case wherein 8 rotation (column rotation) is performed will be described next. The position selecting key 80 is used to set a photographing position at, e.g., $\alpha=30°$, $\beta=30°$, and $\gamma=10°$. Note that the mechanical angles $\alpha$, $\beta$, and $\gamma$ are not limited to the above values but may be set to be other values, respectively. Subsequently, a command signal for commanding the mechanical angles $\alpha$, $\beta$, and $\gamma$ is output to the CPU 68 through the input port 76. A control signal corresponding to the command signal is supplied from the CPU 68 to the C arm controller 90. The C arm 16 is driven by the C arm controller 90 in accordance with the mechanical angles $\alpha$, and $\gamma$. With this operation, the three angles $\alpha$, $\beta$, and $\gamma$ of the C arm 16 are set so that the C arm 16 is located at a desired position of the object 200. The slide angle $\alpha$, the arm rotational angle $\beta$, and the column rotational angle Y are respectively detected by the $\alpha$ angle detecting sensor 64A, the $\beta$ angle detecting sensor 62A, and the $\beta$ angle detecting sensor 60A and the mechanical angles $\alpha$, $\beta$, and $\gamma$ are converted into a digital signal by ADC 70 through the analog multiplexer 66. Subsequently, the diagnostic angles $\theta$ and $\eta$ are calculated as functions of the mechanical angles $\alpha$, $\beta$, and $\gamma$ by the CPU 68 according to equations (1) to (4).

The method of obtaining the diagnostic angles $\theta$ and $\eta$ will be described below with reference to FIGS. 6 and 7. As shown in FIG. 6, the C arm 16 is rotated in the cranial direction through the angle $\beta$, assuming that the amplitude is 1. When the C arm 6 is subsequently rotated in the LAO direction through the angle α, a horizontal component since and a vertical component cosα·sinβ are obtained, as shown in FIG. 7.

Therefore, an amplitude p is given by $$p = \sqrt{\sin^2\alpha + \cos^2\beta \cdot \sin^2\beta}$$

When the amplitude p is rotated about the Z axis through the angle γ, horizontal and vertical components a and b are respectively represented by equations (3) and (4).

In this manner, the diagnostic angles θ and η are respectively obtained as 34.3° and 24.7°. When a memory save button 78 is depressed, a save command signal is input to the CPU 68 through the input port 76. As a result, the CPU 68 writes these diagnostic angles in the memory 72.

In a re-photographing operation, when the reset button 88 is depressed, a command signal for commanding an angle reset operation is input to the CPU 68 through the input port 76. A command signal for setting the rotational angle γ of the Z axis relative to the C arm to be zero is supplied from the CPU 68 to the C arm controller 90. With this operation, the C arm 16 is set at a position where α=34.3°, β=24.7°, and γ=0°.

In addition, the diagnostic angles θ and η are read out from the memory 72 by the CPU 68 and are output to the motor control circuits 82, 84, and 86 through the output port 74. The motors 64, 62, and 60 are respectively rotated by the motor control circuits 82, 84, and 86 in accordance with the diagnostic angles.

As described above, according to this embodiment, when the C arm 16 is rotated about the Z axis to determine a certain photographing direction, the corresponding diagnostic angles are stored in the memory 72. When the diagnostic angles are reproduced from the memory 72, the rotational angle of the C arm 16 with respect to the Z axis is forcibly set to be zero, and the C arm 16 is rotated about other axes, i.e., X and Y axes, to set the diagnostic angles. With this operation, since the mechanical angles of the C arm 16 are uniquely determined with respect to the diagnostic angles, the angles can be quickly reproduced. As a result, the examination time can be shortened, and the operation load of an operator can be reduced.

In order to track a blood vessel during an examination, even if an effective Z-axis rotation is set, since an accurate x-ray radiating direction with respect to the object 200 can always be displayed with diagnostic angles, an operator can recognize a photographing direction of a diagnosis image. With this operation, the positional relationship of the C arm 16 uniquely determined with respect to the diagnostic angles can always be obtained. Therefore, images without rotation can be obtained a plurality of times in a predetermined photographing direction. This improves repeatability of image data. Furthermore, diagnosis precision can also be improved.

Figure 9:
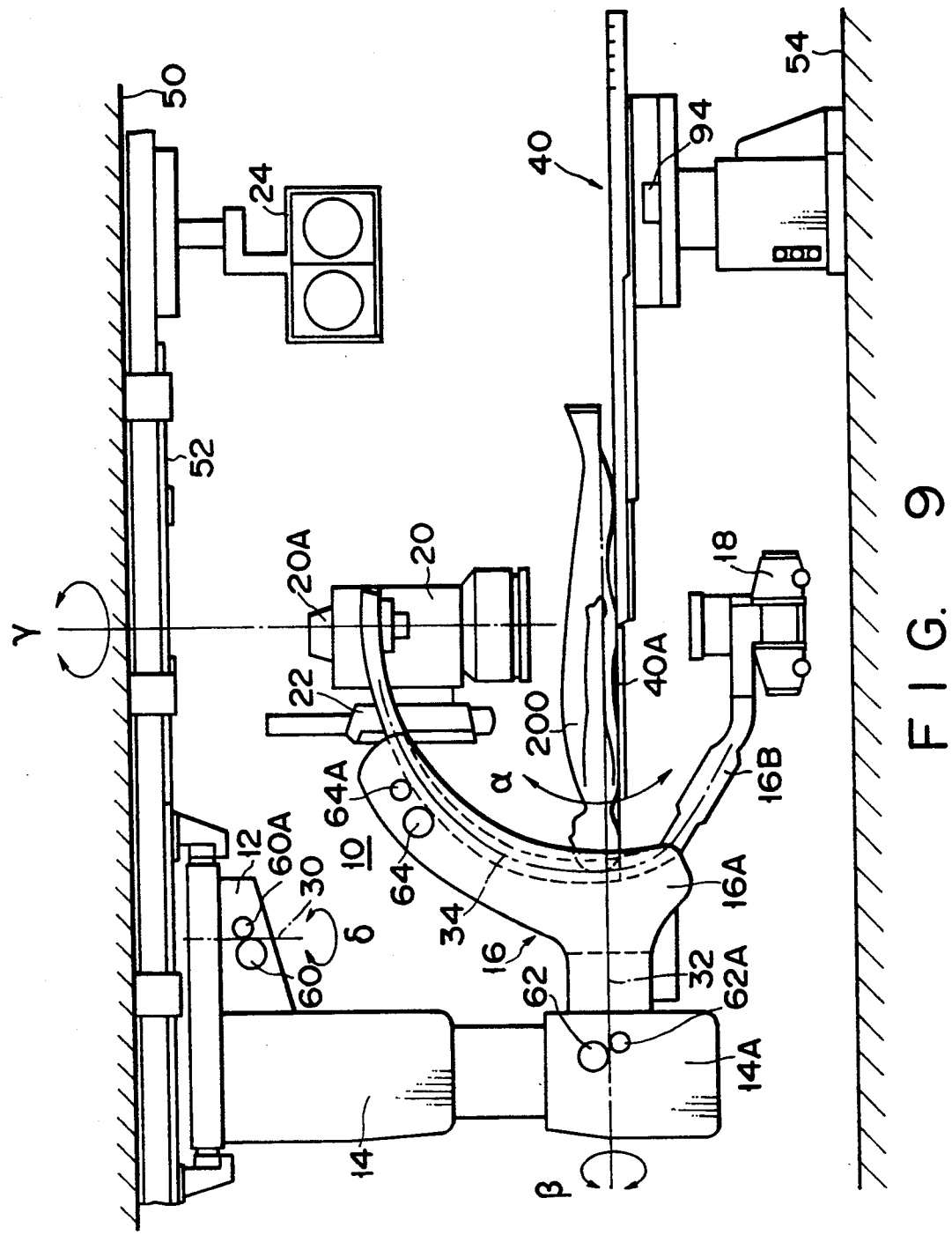
FIG. 9 is a front view showing an x-ray diagnosing apparatus having the control block according to the second embodiment of the present invention.
Figure 10:
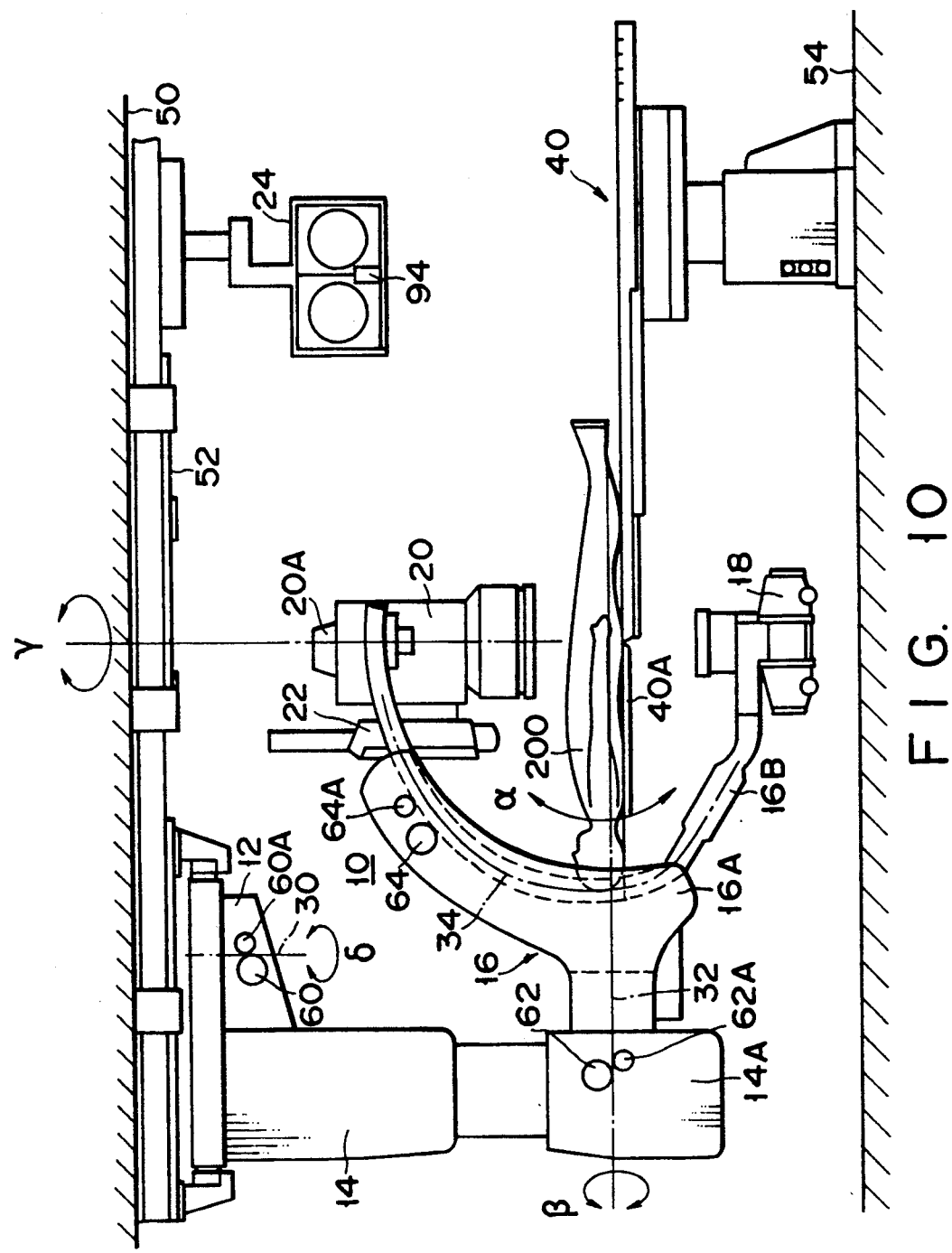
FIG. 10 is a front view showing another x-ray diagnosing apparatus having the control block according to the second embodiment of the present invention.

The second embodiment of the present invention will be described below with reference to FIGS. 8 to 10. As shown in FIG. 8, a CPU 68 controls write and read operations of diagnostic angles with respect to a memory 72, and supplies read diagnostic angles to an I/O port 92 for performing an input/output operation. An angle digital display panel 94 displays the diagnostic angles, i.e., diagnostic angles θ and η, output from the I/O port 92.

The diagnostic angles θ and η obtained in this manner are written in the memory 72 to form a table. With this operation, cumbersome calculations of the diagnostic angles θ and η need not be performed in each angle setting operation. The diagnostic angles θ and η read out from the memory 72 by the CPU 68 are displayed on a digital display panel 94 through the I/O panel 92. The digital display panel 94 is arranged at a position where an operator can easily recognize displayed data. For example, the panel 94 may be arranged on a bed 40, as shown in FIG. 9, or may be arranged on a monitor 24, as shown in FIG. 10.

According to this embodiment, the diagnostic angles θ and η are calculated as functions of mechanical angles α, β, and γ detected by sensors 60A, 62A, and 64A by using the above-mentioned calculations. As a result, accurate diagnostic angles uniquely defined as a photographing direction can be obtained and can be displayed on the angle digital display panel 94. Even if the angle γ is set, since an accurate x-ray radiating direction with respect to an object 200 to be examined can always be displayed with diagnostic angles, an operator can recognize a photographing direction of a diagnosis image. With this operation, an angle setting operation can be quickly performed to shorten the time required for examination, thus reducing the operation load of the operator. In addition, images can be obtained a plurality of times in a predetermined photographing direction. That is, repeatability of image data can be improved, and diagnosis precision ca be improved.

In the above-described embodiments, each holding unit having a C arm has been described. However, a holding unit may have a U arm and may have another shape. Furthermore, in the above embodiments, the Z-axis rotational angle about the Z axis is set to be 90°. However, other angles may be set.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An x-ray diagnosing apparatus comprising:
  a holding unit including a base which can be moved on rails installed on a ceiling and includes a column rotation axis for setting a column rotational angle γ and a sensor for detecting the column rotational angle γ,
  a column which has one end fixed to said base and includes a spindle rotational axis for setting an arm rotational angle β and a sensor for detecting the arm rotational angle β,
  an arm which is fixed to the other end of said column and includes a slide axis for setting a slide angle α and a sensor for detecting the slide angle α,
  x-ray generating means fixed to one end of said arm, and
  x-ray image detecting means fixed to the other end of said arm;
  calculating means for calculating clinically defined diagnostic angles θ and η by using the rotational angles α, β and γ, and said diagnostic angle θ is $\tan^{-1}b/\sqrt{1-(a^2+b^2)}$, and the diagnostic angle $\eta$ is $\sin^{-1}a$, where $$a = \sqrt{\sin^2\alpha + \cos^2\alpha \cdot \sin 2\beta} \cdot \cos\{\gamma + \sin^{-1}(\sin\beta/\tan\alpha)\}$$

and $$b = \sqrt{\sin^2\alpha + \cos^2\alpha \cdot \sin^2\beta} \cdot \sin\{\gamma + \tan^{-1}(\sin\beta/\tan\alpha)\};$$

storage means for storing the diagnostic angles calculated by said calculating means; and control means for performing write control to write the diagnostic angles, of said holding unit in a photographing operation, in said storage means, performing read control to read out the diagnostic angles from said storage means in a re-photographing operation, and performing control to supply a command to said rotating/driving means to set said holding unit in the same state as in the photographing operation by using the diagnostic angles read out by the read control.

2. An apparatus according to claim 1, wherein said x-ray image detecting means includes an image intensifier, a film changer, and a cinematic camera.

3. An apparatus according to claim 1, wherein said control system includes position setting means for setting said holding unit at one of a plurality of predetermined positions.

4. An x-ray diagnosing apparatus comprising:

a holding unit including a base which can be moved on rails installed on a ceiling and includes a column rotation axis for setting a column rotational angle $\gamma$ and a sensor for detecting the column rotational angle $\gamma$, a column which has one end fixed to said base and includes a spindle rotation axis for setting an arm rotational angle $\beta$ and a sensor for detecting the arm rotational angle $\beta$, an arm which is fixed to the other end of said column and includes a slide axis for setting a slide angle $\alpha$ and a sensor for detecting the slide angle $\alpha$, x-ray generating means fixed to one end of said arm, and x-ray image detecting means fixed to the other end of said arm;

calculating means for calculating clinically defined diagnostic angles $\theta$ and $\eta$ by using the rotational angles $\alpha$, $\beta$ and $\gamma$, and said diagnostic angle $\theta$ is $\tan^{-1}b/\sqrt{1-(a^2+b^2)}$, and the diagnostic angle $\eta$ is $\sin^{-1}a$, where $$a = \sqrt{\sin^2\alpha + \cos^2\alpha \cdot \sin 2\beta} \cdot \cos\{\gamma + \sin^{-1}(\sin\beta/\tan\alpha)\}$$

and $$b = \sqrt{\sin^2\alpha + \cos^2\alpha \cdot \sin^2\beta} \cdot \sin\{\gamma + \tan^{-1}(\sin\beta/\tan\alpha)\};$$

storage means for storing the diagnostic angles calculated by said calculating means; and control means for performing write control to write the diagnostic angles, of said holding unit in a photographing operation, in said storage means, and performing read control to read out the diagnostic angles from said storage means in a re-photographing operation; and display means for displaying the diagnostic angles read out from said control means.

5. An apparatus according to claim 4, wherein said x-ray image detecting means is at least one of an image intensifier, a film changer, and a cinematic camera.

6. An apparatus according to claim 4, wherein said control system includes position setting means for setting said holding unit at one of a plurality of predetermined positions.

7. An apparatus according to claim 4, further comprising a table unit for setting an object, said display means is arranged on the table unit.

8. An apparatus according to claim 4, further comprising a monitor TV for displaying an x-ray image, said display means is arranged on a monitor TV.

* * * * *